(12) United States Patent
Worrell

(10) Patent No.: US 10,743,899 B2
(45) Date of Patent: Aug. 18, 2020

(54) SURGICAL INSTRUMENT WITH ARTICULATING AND ROTATING END EFFECTOR AND FLEXIBLE COAXIAL DRIVE

(71) Applicant: Ethicon LLC, Guaynabo, PR (US)

(72) Inventor: Barry Worrell, Centerville, OH (US)

(73) Assignee: Ethicon LLC, Guaynabo, PR (US)

( * ) Notice: Subject to any disclaimer, the term of this patent is extended or adjusted under 35 U.S.C. 154(b) by 333 days.

(21) Appl. No.: 15/468,458

(22) Filed: Mar. 24, 2017

(65) Prior Publication Data

US 2018/0271553 A1 Sep. 27, 2018

(51) Int. Cl.
| A61B 17/295 | (2006.01) |
| A61B 17/29 | (2006.01) |
| A61B 18/14 | (2006.01) |
| A61B 18/00 | (2006.01) |

(52) U.S. Cl.
CPC ............ *A61B 17/295* (2013.01); *A61B 17/29* (2013.01); *A61B 18/1445* (2013.01); *A61B 2017/2927* (2013.01); *A61B 2017/2929* (2013.01); *A61B 2018/00404* (2013.01); *A61B 2018/00607* (2013.01); *A61B 2018/1455* (2013.01)

(58) Field of Classification Search
CPC .......... A61B 17/295; A61B 17/320016; A61B 17/3205; A61B 17/29; A61B 2017/2927; A61B 2017/2929; A61B 18/1445; A61B 2018/00404; A61B 2018/00607; A61B 2018/1455
See application file for complete search history.

(56) References Cited

U.S. PATENT DOCUMENTS

| 9,161,803 | B2 | 10/2015 | Yates et al. | |
| 9,848,878 | B2* | 12/2017 | Racenet | A61B 17/068 |
| 2008/0294166 | A1* | 11/2008 | Goldin | A61B 17/1617 606/79 |
| 2011/0106073 | A1* | 5/2011 | Mueller | A61B 17/29 606/41 |
| 2011/0230875 | A1* | 9/2011 | Walberg | A61B 17/29 606/33 |
| 2012/0083835 | A1 | 4/2012 | Shelton, IV et al. | |
| 2013/0161374 | A1 | 6/2013 | Swayze et al. | |
| 2014/0276719 | A1 | 9/2014 | Parihar | |
| 2016/0270809 | A1* | 9/2016 | Boudreaux | A61B 17/295 |
| 2017/0071618 | A1* | 3/2017 | Hsu | A61B 17/29 |

* cited by examiner

*Primary Examiner* — Kathleen S Holwerda
*Assistant Examiner* — Brooke Labranche
(74) *Attorney, Agent, or Firm* — Mintz Levin Cohn Ferris Glovsky and Popeo, P.C.

(57) ABSTRACT

Surgical instruments having articulating and rotating end effectors utilizing a flexible coaxial drive are described herein. In one embodiment, a surgical instrument is provided that includes a shaft and an end effector coupled to a distal end of the shaft by an articulation joint such that the end effector can articulate relative to a longitudinal axis of the shaft and can rotate about a longitudinal axis of the end effector. The instrument can further include an actuating cable coaxially disposed within a lumen of the shaft and extending through the articulation joint to the end effector. The actuating cable can be configured to bend and rotate through the articulation joint. Further, rotation of the actuating cable can be configured to control a first function of the end effector and translation of the actuating cable can be configured to control a second function of the end effector.

30 Claims, 9 Drawing Sheets

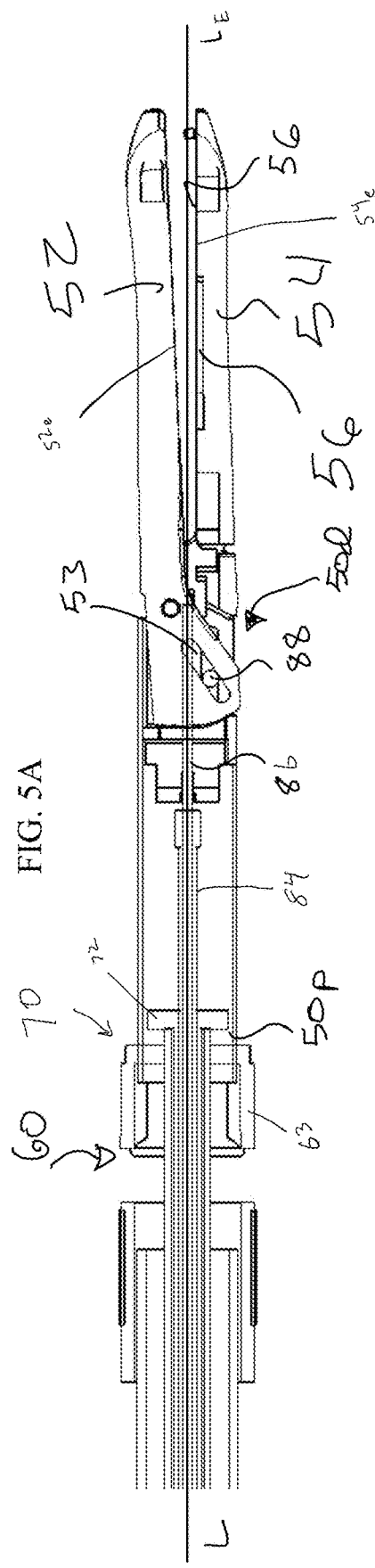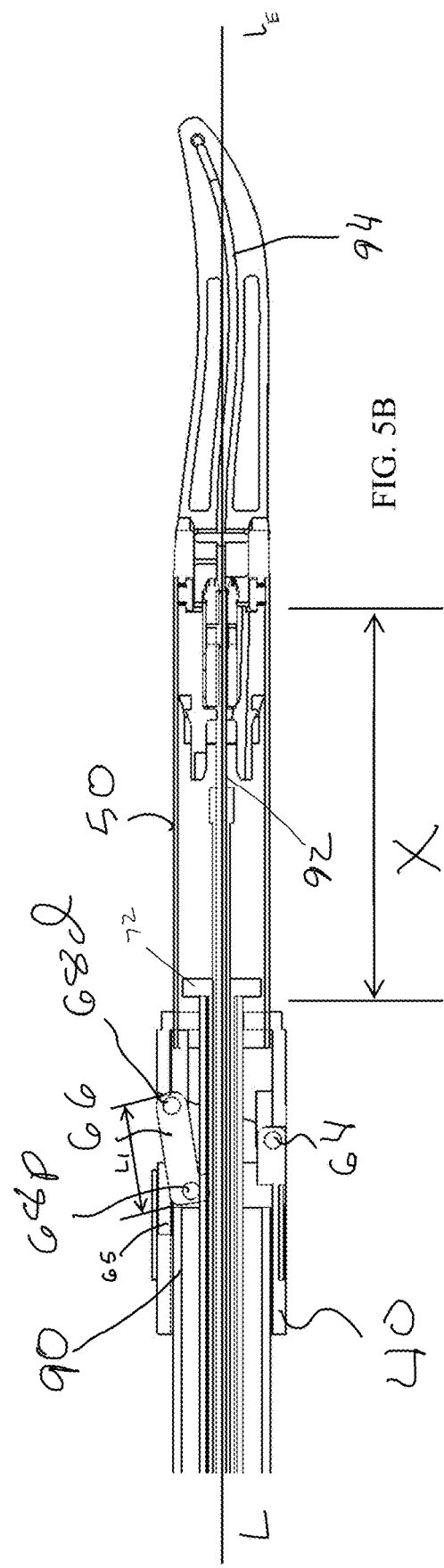

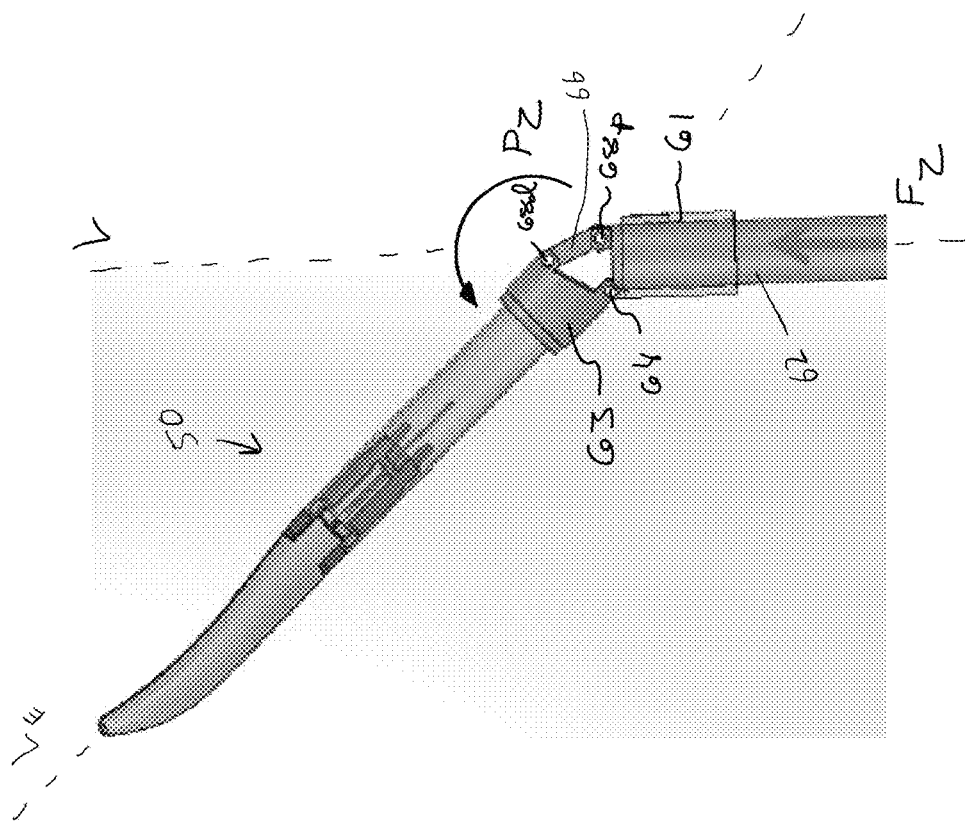
FIG. 6C
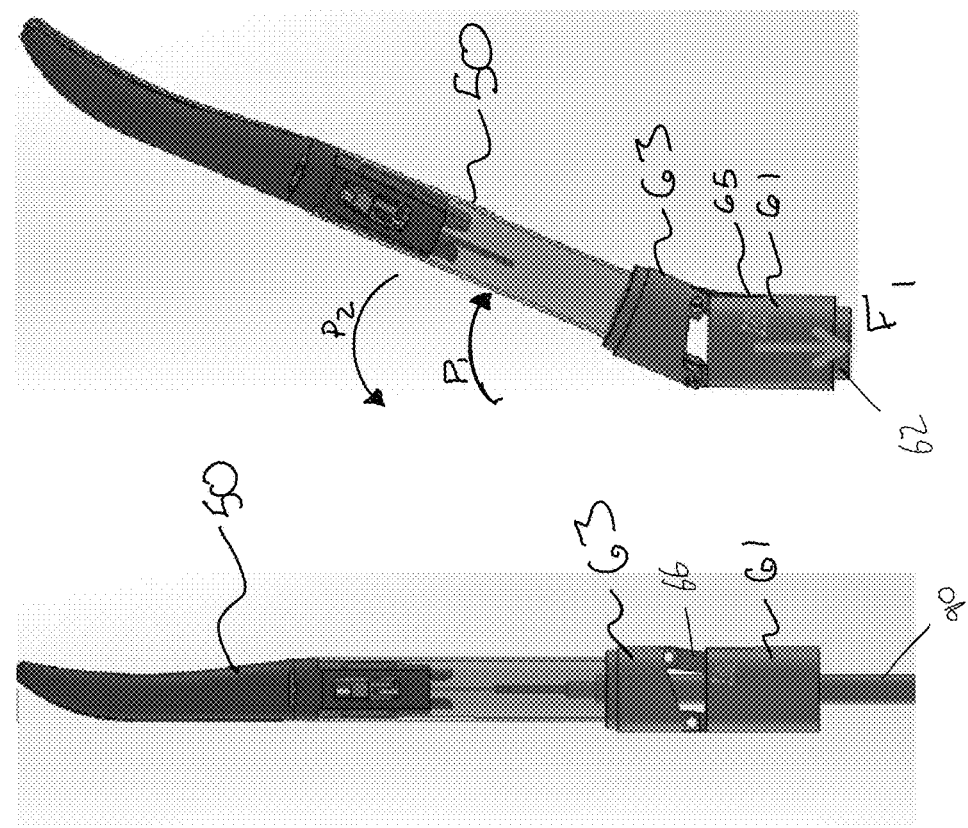
FIG. 6B
FIG. 6A

SURGICAL INSTRUMENT WITH ARTICULATING AND ROTATING END EFFECTOR AND FLEXIBLE COAXIAL DRIVE

FIELD

This disclosure relates generally to surgical instruments and, more particularly, to such instruments that include articulating and rotating end effectors to allow relative position changes between the end effector and other portions of the instrument.

BACKGROUND

Surgical instruments are used in various open, endoscopic, and laparoscopic surgeries to perform a variety of tasks. Certain surgical instruments utilize an end effector to manipulate tissue. For example, instruments can include an end effector that can grasp tissue and, in some cases, seal and transect tissue volumes and blood vessels. Some such instruments or devices can generally include opposed jaws for grasping tissue and can also include a cutting mechanism that can be advanced through grasped tissue to transect it. In some instances, the devices can also be configured to apply electrical or other energy to the grasped tissue to seal it before tissue transection is completed. For example, various mono-polar and bi-polar radio frequency (RF) surgical instruments and associated techniques have been developed for sealing tissue volumes and blood vessels. Such devices often utilize electrodes disposed on a face of one or both of the jaws to deliver electrical or other energy to the grasped tissue.

Certain devices can also include the ability to articulate a distal end of the device, such as the jaws or other end effector components. An articulating distal end can allow the jaws or other end effector to be manipulated off a central longitudinal axis of the device to access, or more easily access, areas of a surgical site that would otherwise be difficult or impossible to reach if the end effector were in fixed alignment with a shaft of the device. Further, some such devices can additionally include the ability to rotate the end effector of the device around a central longitudinal axis thereof to reorient the end effector. In some cases, it can be desirable to maintain an ability to rotate the end effector even after it has been articulated into a position offset from a longitudinal axis of the device.

Implementing the ability to rotate an end effector about a central axis thereof, even after articulating the end effector relative to a surgical instrument, can introduce challenges. For example, after the end effector has been articulated and/or rotated, actuating cables extending to the end effector can fail due to kinking, twisting, or other deformation. As a result, additional mechanisms can be required to prevent such failure, but these mechanisms can themselves introduce complexity and potential failure points.

By way of further example, in prior devices slip rings have been utilized to transfer electrical energy to an end effector in a manner that is not susceptible to twisting due to rotation. These components, however, can be more complex, more prone to failure, and less efficient than, e.g., a continuous wire conductor. In another example, rigid shafts utilized to effect rotation of an end effector cannot be employed with an end effector that both rotates and articulates, as the shaft cannot bend through the articulation joint. In still another example, prior devices have included articulation mechanisms that utilize a plurality of control bands to effect articulation, such as oppositely-disposed bands configured to operate in a "push/pull" manner to cause articulation in one direction or another. Some prior articulation mechanisms have further utilized a structure of segmented beads that function similarly to a series of ball-and-socket joints to allow articulation of an end effector. These devices can be complex, expensive, and prone to buckling in certain maneuvers, such as distal advancement and other maneuvers in which the instrument experiences axial compression forces. They also can result in larger devices (e.g., due to the numerous components, such as multiple articulation control bands, components to allow for rotation of the end effector without kinking or twisting, etc.) that are less desirable for certain minimally invasive procedures in which the instrument is introduced through an incision or access port of limited size.

Accordingly, there is a need for improved surgical instruments having articulating and rotating end effectors that have reduced size, complexity, susceptibility to failure, and increased strength, e.g., in axial compressive loading.

SUMMARY

The present disclosure generally relates to surgical instruments and methods that provide both articulation and rotation of a distal end effector using a flexible coaxial drive that can actuate various functions of the end effector regardless of how much the end effector is articulated and/or rotated with respect to an elongate shaft to which it is coupled and/or from which it extends. In the illustrated embodiments, the end effectors include jaw assemblies that are articulable and rotatable with respect to an elongate shaft of the device. The instruments disclosed herein also provide features that allow the surgical instruments to grasp tissue, cut tissue grasped by the end effector using a cutting mechanism, and seal the grasped and/or transected tissue using one or more electrodes in any articulated configuration attainable by the instrument. Alternatively, the end effectors disclosed herein can be configured to perform any combination of the aforementioned functions, such as grasping and cutting without sealing, or grasping alone. Moreover, the embodiments described herein can include improved articulation control mechanisms that can include a single actuating member that can be used to control articulation about a pivot axis defined by a hinge.

In one aspect, a surgical instrument is provided that can include a shaft having a proximal end, a distal end, and lumen extending therethrough, as well as an end effector coupled to the distal end of the shaft by an articulation joint such that the end effector can articulate relative to a longitudinal axis of the shaft and can rotate about a longitudinal axis of the end effector. The instrument can further include an actuating cable coaxially disposed within the lumen of the shaft and extending through the articulation joint to the end effector. The instrument can also include an articulation control shaft coaxially disposed within the lumen of the shaft and configured to translate proximally and distally to articulate the end effector relative to the longitudinal axis of the shaft. The actuating cable can be configured to bend and rotate through the articulation joint, and rotation of the actuating cable can be configured to control a first function of the end effector and translation of the actuating cable can be configured to control a second function of the end effector.

The instruments and methods described herein can have a number of additional features and/or variations, all of which are within the scope of the present disclosure. In some embodiments, for example, the first function can be rotation of the end effector about a longitudinal axis thereof. Moreover, in some embodiments the end effector can include a first jaw and a second jaw pivotally coupled to one another and movable between an open configuration and a closed configuration. In such an embodiment, the second function can be moving the first and second jaws between the open and closed configurations. In other embodiments, the end effector can include a first jaw and a second jaw pivotally coupled to one another and movable between an open configuration and a closed configuration, as well as a blade configured to translate proximally and distally relative to the first and second jaws. In such an embodiment, the second function can be translating the blade to transect tissue grasped between the first and second jaws. In such an embodiment, the instrument can further include a jaw closure cable coaxially disposed within the actuating cable and configured to translate proximally and distally to move the first and second jaws between the open and closed configurations. Still further, in some embodiments the instrument can further include a conductor coaxially disposed within the jaw closure cable and configured to deliver energy to the end effector. In certain embodiments, the articulation control shaft can be coaxially disposed about the actuating cable within the lumen of the shaft.

In other embodiments, the articulation joint can include a distal portion rotatably coupled to the end effector and a proximal portion coupled to the shaft, and the distal portion can be coupled to the proximal portion by a hinge pin that is offset from the longitudinal axis of the shaft. In such an embodiment, the articulation control shaft can be coupled to the distal portion of the articulation joint at a position oppositely offset from the longitudinal axis of the shaft. In some embodiments, the hinge pin can be positioned along an outer circumference of the articulation joint. In other embodiments, the instrument can further include an elongate link extending between the articulation control shaft and the distal portion of the articulation joint. Further, the proximal portion of the articulation joint can include a slot extending proximally from a distal end thereof and sized to receive the elongate link when the end effector is articulated relative to the shaft. Still further, in some embodiments the hinge pin can be positioned proximal to a distal end of the elongate link when the longitudinal axis of the end effector is aligned with the longitudinal axis of the shaft.

The above-described instrument, and other embodiments described herein, can be configured for use by a surgeon or other user directly. For example, in some embodiments the instrument can include an interface coupled to the proximal end of the shaft and configured to control rotation and translation of the actuating cable. The interface can, in some embodiments, include a pistol grip handle with one or more triggers or other actuators that a user can manipulate to control functions of the end effector. In other embodiments, however, the instrument can include an interface configured for use with a surgical robot, such that the instrument can be incorporated into any of a variety of surgical robot systems.

In another aspect, a surgical instrument is provided that can include an elongate cylindrical housing having a proximal end, a distal end, and a lumen extending therethrough along a longitudinal axis. The instrument can further include an end effector coupled to the distal end of the housing by a hinge mechanism including a hinge pin that is offset from the longitudinal axis of the housing, and a coaxial member extending through the lumen and the hinge mechanism to the end effector. The surgical instrument can have a first configuration in which the elongate cylindrical housing and the end effector are substantially coaxially aligned, and a second configuration in which the end effector is pivoted relative to the elongate cylindrical housing such that the end effector is angularly offset from the longitudinal axis. Further, the coaxial member can be configured to bend and rotate within the hinge mechanism when the surgical instrument is in the second configuration, and rotation of the coaxial member can be configured to control a first function of the end effector and translation of the coaxial member can be configured to control a second function of the end effector.

As with the instrument described above, a number of variations and additional features are possible. For example, in some embodiments the hinge mechanism can include a push-pull mechanism. The push-pull mechanism can include a distal end and a proximal end, and can be coaxially disposed between the housing and the coaxial member in certain embodiments. Still further, the hinge pin can pivotally connect a first side of the end effector to the housing, and the hinge mechanism can further include a second hinge pin pivotally connecting a second side of the end effector to the push-pull mechanism. And, in some embodiments, the hinge pin can be proximal to the second hinge pin when the instrument is in the first configuration. In certain embodiments, the hinge mechanism can include an elongate link disposed between the second hinge pin and the distal end of the push-pull mechanism. Moreover, the push-pull mechanism can be configured to actuate the surgical instrument from the first configuration to the second configuration with substantially linear movement of the push-pull mechanism in certain embodiments.

In other embodiments, the coaxial member can include at least an inner member and an outer member, the end effector can include a grasper and a knife, and the inner member can be configured to actuate the grasper and the outer member can be configured to actuate the knife. In certain embodiments, the inner and outer members can be configured to slide along the longitudinal axis within the elongate cylindrical housing and the hinge mechanism while the surgical implement is in the second configuration to actuate the grasper and the knife. Moreover, in some embodiments, the instrument can further include a substantially cylindrical guide disposed around the inner member and connected to a grasper actuation link. The guide can have a slot extending therethrough for receiving a distal end of the knife such that the knife can slide within the slot.

In another aspect, a surgical method is provided that can include articulating an end effector relative to a shaft by translating a single articulation control shaft coaxially disposed within the shaft. The method can further include rotating the end effector about a longitudinal axis thereof by rotating an actuating cable coaxially disposed within the articulation control shaft, and actuating an end effector function by translating the actuating cable.

As with the devices described above, surgical methods disclosed herein can include a number of variations and/or additional steps. For example, in some embodiments the method can further include actuating a second end effector function by translating a second actuating cable coaxially disposed within the actuating cable. In certain embodiments, the end effector function can be translation of a blade to transect tissue and the second end effector function can be movement of first and second jaws of the end effector to capture tissue.

Moreover, in certain embodiments the method can further include delivering energy to tissue grasped by the first and second jaws through a conductor coaxially disposed within the second actuating cable.

Any of the features or variations described above can be applied to any particular aspect or embodiment of the disclosure in a number of different combinations. The absence of explicit recitation of any particular combination is due solely to the avoidance of repetition in this summary.

BRIEF DESCRIPTION OF THE DRAWINGS

FIG. 5A is a side cross-sectional view of the surgical instrument of FIG. 1;

FIG. 5B is a top cross-sectional view of the surgical instrument of FIG. 1;

FIG. 6A is a partial top view of the surgical instrument of FIG. 1 in a first configuration;

FIG. 6B is a partial top view of the surgical instrument of FIG. 1 in a second configuration;

FIG. 6C is a partial top view of the surgical instrument of FIG. 1 in a third configuration;

DETAILED DESCRIPTION

Figure 1:
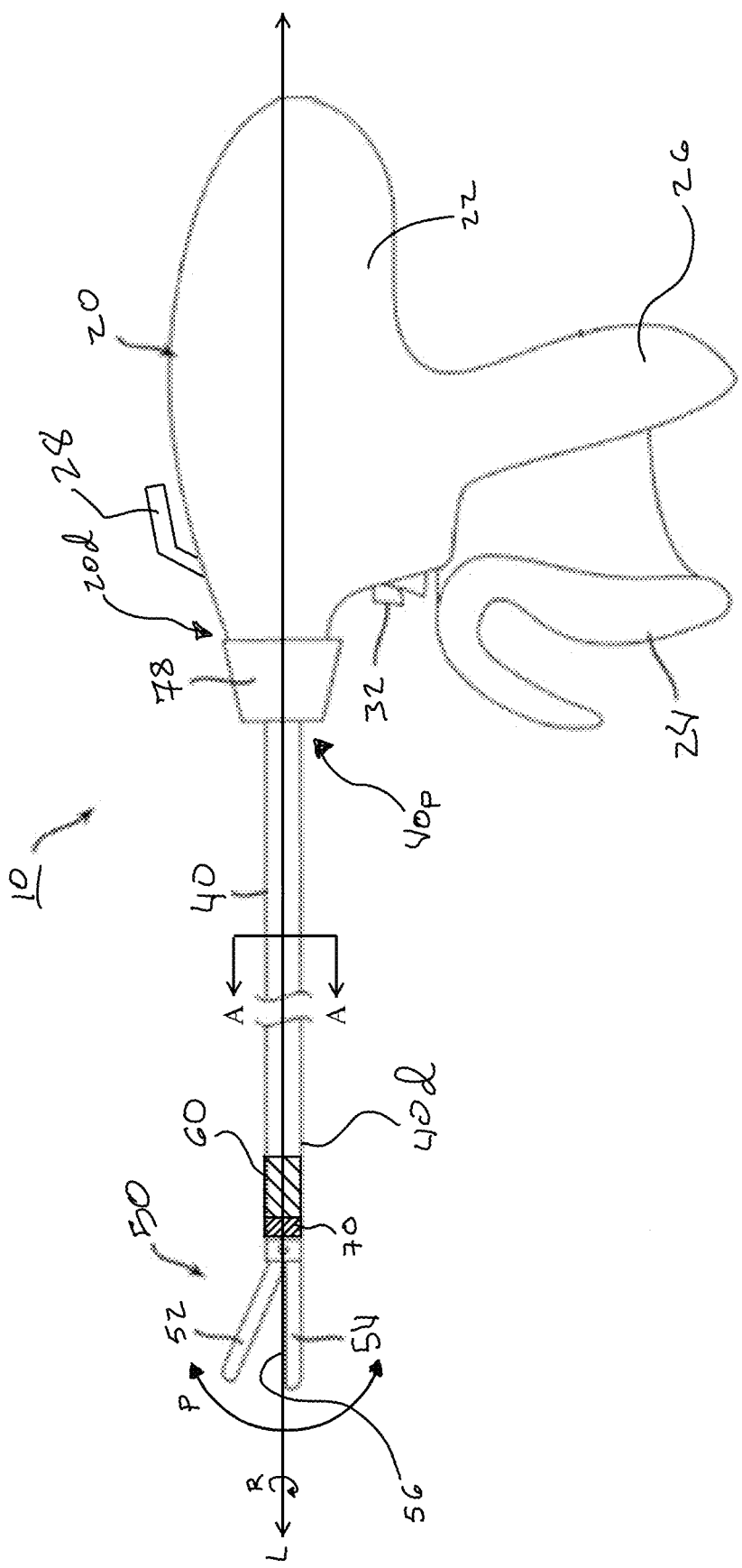
FIG. 1 is a side schematic view of one embodiment of a surgical instrument according to the teachings of the present disclosure.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. To the extent that features are described as being a "first feature" or a "second feature," such numerical ordering is generally arbitrary, and thus such numbering can be interchangeable.

Additionally, to the extent that linear or circular dimensions are used in the description of the disclosed instruments and methods, such dimensions are not intended to limit the types of shapes that can be used in conjunction with the disclosed instruments and methods. A person skilled in the art will recognize that an equivalent to such linear and circular dimensions can easily be determined for any geometric shape. Still further, sizes and shapes of the instruments, and the components of those instruments, can depend at least on the anatomy of the subject in which the instruments will be used, the size and shape of components with which the instruments will be used, and the methods and procedures in which the instruments will be used.

The present disclosure generally relates to surgical devices and methods for articulating and rotating an end effector of a surgical device that allows the end effector to perform consistently regardless of how much the end effector is articulated and rotated with respect to an elongate shaft from which it is coupled to and/or from which it extends. In the illustrated embodiments, the end effectors are jaw assemblies that are articulable and rotatable with respect to an elongate shaft of the device, and the disclosures provide for features that allow the surgical device to grasp tissue with the jaws, cut tissue disposed between the jaws using a cutting mechanism that travels through the jaws, and seal the tissue disposed between the jaws using one or more electrodes associated with the jaws in any articulated configuration attainable by the device. Alternatively, the end effector can be configured to perform any combination of the aforementioned functions, for example grasping and cutting without sealing. The tissue with which the devices provided for herein can be used can include tissue or blood vessels, collectively referred to herein as "tissue." The devices described herein can include an articulation joint designed to be actuated by a single control (e.g., a shaft, cable, etc.) that extends through a lumen of the elongate shaft while providing for rotation of the end effector and associated actuating cables that extend through the articulation joint to the end effector. Rotation of the end effector about the longitudinal axis can be achieved by rotating one or more of these coaxially disposed actuating cables or controls extending through the articulation joint to the end effector. Further, end effector functions, such as jaw closure, tissue grasping, tissue transection, and tissue sealing can be performed at any degree of articulation and/or rotation due to the use of flexible and rotatable coaxial drive cables, members, or controls that are configured to bend and rotate through the articulation joint.

FIG. 1 illustrates one embodiment of a surgical instrument 10 according to the teachings of the present disclosure. The surgical instrument 10 can be configured to grasp, seal, and transect tissue, and generally extends along a longitudinal axis L. The surgical instrument 10 can include an operator interface 20, an outer elongate shaft 40, an end effector 50, an articulation joint 60 for articulating the end effector relative to the shaft, and a rotation joint 70 for rotating the end effector relative to the shaft.

Figure 2:
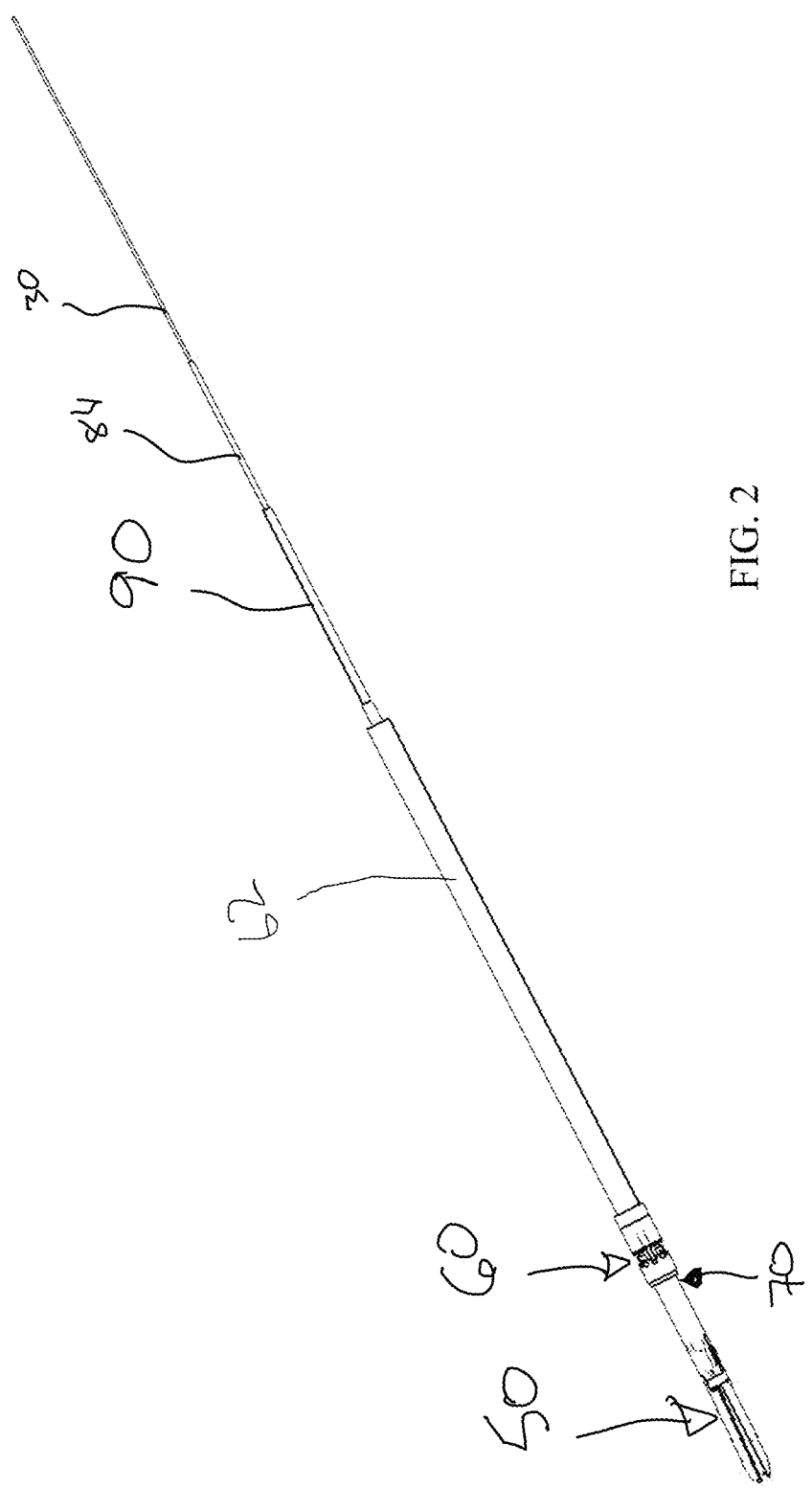
FIG. 2 is a partial perspective view of the surgical instrument of FIG. 1.
Figure 3:
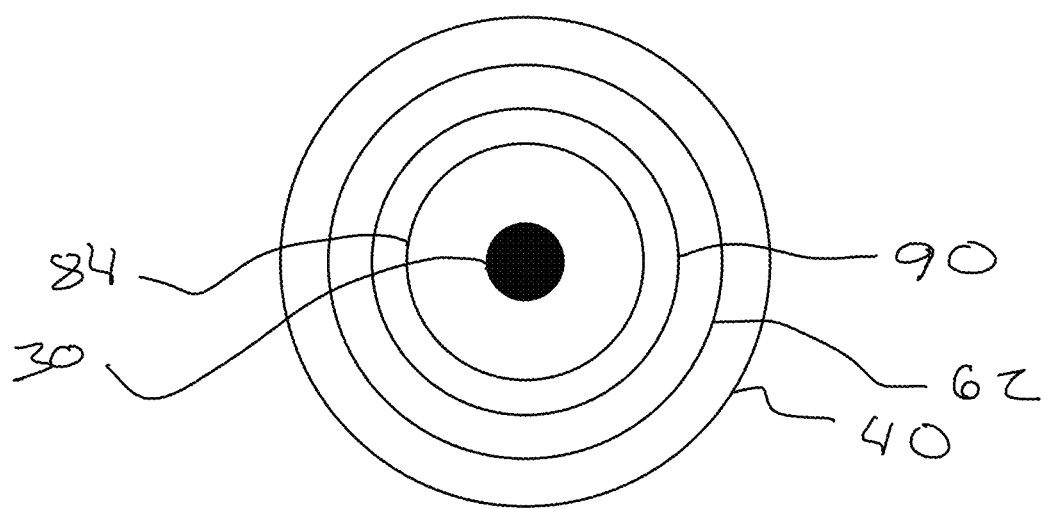
FIG. 3 is a cross-sectional view of the surgical instrument of FIG. 1 along the line A-A.

The operator interface 20 can have a variety of forms and can be configured to provide one or more actuators that can control functions of the end effector 50. In the illustrated embodiment, the interface 20 can be configured for use by a surgeon or other human user. For example, the interface 20 can include a trigger 24 and a handle 26 that can be utilized to close and open a jaw assembly of the end effector 50 to grasp tissue. The jaw assembly can include a first jaw 52 and a second jaw 54 that are configured to pivot with respect to one another to grasp tissue disposed therebetween. Moreover, in some non-limiting embodiments, the end effector 50 can include a blade 92 (see FIG. 4) to transect tissue grasped by the jaws 52, 54. By way of further non-limiting example, the operator interface 20 can control the supply of electrical energy to one or more electrodes 56 associated with any of the jaws 52, 54 or other end effector components to weld, coagulate, and/or seal portions of the grasped tissue. Other components involved in tissue sealing, such as a power source (not shown), etc., can be disposed in the operator interface 20 and can extend through or be electrically or mechanically coupled to components that extend through the shaft 40. In some embodiments, for example, a conductor 30, such as one or more cables, wires, or leads (see FIGS. 2 and 3), can be utilized to conduct electrical energy from the interface 20 to the end effector 50. Further, the interface 20 can include further controls to actuate other functions of the end effector 50, including, for example, an articulation control 62, a jaw closure control 84, and a transection control 90, as shown in FIGS. 2 and 3. As discussed in greater detail below, the articulation control 62 can be a shaft, cable, or other element used to articulate the end effector 50 with respect to the shaft 40, the closure control 84 can be a shaft, cable, or other element used to open or close the jaws 52, 54, the transection control 90 can be a shaft, cable, or other element configured to transect tissue grasped by the jaws using the blade 92, and the conductor 30 can be configured to selectively deliver electrical energy to tissue grasped by the jaws via the electrodes 56. The conductor 30, the closure control 84, and the transection control 90 can sometimes be collectively referred to herein as the "end effector operational components," and can collectively extend through both the shaft 40 and the articulation joint 60 to couple to the end effector 50. These components can also be configured to both bend and rotate through the articulation joint 60.

The operator interface 20 can have any type of design known in the art for controlling an end effector 50. As shown in the illustrated embodiment, the interface 20 can have a pistol-grip configuration that includes a housing 22, an actuating trigger 24, and a stationary handle 26. Movement of the actuating trigger 24 towards the stationary handle 26 can effect a variety of functions. The interface 20 can be sized and shaped ergonomically for handheld use by a surgeon or other operator. The housing 22 and other components of the interface 20 can be constructed from any material or combination of materials that is suitable for use in a surgical instrument that can be directly manipulated by a user.

The interface 20 can also include an articulation handle or lever 28 for articulating the end effector 50 relative to the shaft 40 via the articulation joint 60. As shown, the articulation lever 28 can be disposed at a distal end 20*d* of the interface 20, for instance on a top portion of the handle portion 20. The articulation lever 28 can be manipulated from side-to-side along a surface of the interface 20 (as shown, into and out of the page) to facilitate reciprocal articulation of the end effector 50. A variety of other configurations of an articulation lever, as well as other components that can be associated with an interface 20 to effect articulation of the end effector 50 instead of, or in conjunction with, the articulation lever 28 are possible and considered within the scope of the present disclosure.

The mechanical and electrical components associating the articulation control 62, closure control 84, and transection control 90 with the actuating trigger 24 and the articulation lever 28, respectively, can be disposed in the housing 22 and the outer elongate shaft 40, including drivers, controllers, and levers, among other components. For example, a driver can be a motor in some embodiments, such as a pneumatic motor, a hydraulic motor, and/or a solenoid, disposed within the housing 22 of the interface 20 and used to power any of the end effector operational components. Other configurations are also possible for actuating the jaws 52, 54, the closure control 84, the articulation control 62, and/or the transection control 90 and can include, but are not limited to, actuator levers, triggers, knobs, and sliders. Further, there are a variety of other functions that the actuating trigger 24 and/or articulation lever 28, or other actuators or controls, can perform that are considered within the scope of the present disclosure.

The illustrated embodiment can also include a tissue sealing control or actuator, e.g., a button 32, as part of the interface 20. The button 32 can be configured such that it selectively completes a circuit to deliver electrical energy to tissue grasped by the jaws 52, 54 via the one or more electrodes 56 and the conductor 30 coupled between the electrode and a driver or power source. This energy can be utilized to seal tissue disposed between the jaws 52, 54. More particularly, completion of a circuit by depressing the button 32 can allow electrical energy to pass from a power source disposed in the housing 22, through the conductor 30, and to the one or more electrodes 56. The conductor 30 can be disposed in the shaft 40 to electrically couple the button 32 and the electrodes 56. Although the power source can be disposed in the housing 22 in some embodiments, in other embodiments the power source can be external of the housing 22 and the instrument 10 can be configured to electrically connect to the power source, for instance by way of a socket extending from the housing 22 to connect to the power source. As with the actuating trigger 24, the button 32 can have a variety of other configurations and can perform a variety of other functions, all of which are considered within the scope of the present disclosure.

Other features to assist in moving and actuating the components of the device 10 can also be incorporated into the interface 20. By way of example, the interface 20 can include a rotation control 78, such as a rotatable knob or ring, disposed at a distal end 20*d* of the interface 20 to facilitate rotation of the end effector 50 via the rotation joint 70. Actuation of the rotation joint 70 can cause rotation of the end effector 50 with respect to the interface 20 and shaft 40 around a centrally disposed longitudinal axis L of the shaft 40. As in the illustrated embodiment, the rotation control 78 can be approximately adjacent to the articulation lever 28, although other locations for these components are possible. Other non-limiting examples of features that can be incorporated into the interface 20 to assist in manipulating or otherwise operating the device 10 can include: (1) a retraction handle for retracting the cutting blade 92 towards and/or to its initial position in place of, or independent of, any retraction that is part of a firing stroke initiated by the actuating trigger 24; (2) a firing lockout assembly to prevent the cutting blade 92 from being actuated at an undesirable time; and (3) an emergency return button to retract the cutting blade 92 before a firing stroke is completed, for instance in a case where completing the firing stroke may cause tissue to be undesirably cut.

Although features such as a retraction handle, a firing lockout assembly, and an emergency return button are not explicitly illustrated in the device 10, a number of configurations for each feature are known and can be incorporated into the interface 20 and/or other portions of the device 10 without departing from the spirit of the present disclosure. In addition, the teachings of the present disclosure can be applied to different types of tissue-grasping surgical instruments, including, for example, motorized devices like those described in U.S. Pat. No. 9,161,803, as well as instruments configured for use with surgical robots like those described in U.S. Pat. Pub. No. 2014/0276719. The teachings of each of these references are incorporated by reference in their entirety.

While the embodiment of a surgical instrument illustrated in FIG. 1 is configured for use by a surgeon or other user, such an instrument can also include an interface 20 configured such that its various components can be operated, for example, through various electrical and/or robotic controls, rather than by hand. Movement or other use of any end effector operational component, the jaws 52, 54, the cutting blade 92, and the one or more electrodes 56 can be achieved by electrical and/or robotic controls. For example, a surgical robot can actuate an end effector 50 via a coupling between the shaft 40 and a robot arm or via a robotic interface for operating the handle, trigger, switches, etc. of an instrument like the one illustrated in FIG. 1.

The outer elongate shaft 40 can be coupled to the distal end 20d of the handle portion 20 at a proximal end 40p of the shaft 40 and can include a bore or lumen (not shown) extending through the shaft 40 for passing mechanisms to help actuate various functions of the end effector 50, or to perform other functions at the surgical site, such as cutting or delivering electrical energy for sealing. As noted above, while the illustrated embodiment shows various end effector operational components disposed through the shaft 40, the device 10 can include only a subset of such operational components in various embodiments, depending upon the functionality of the included end effector. The outer elongate shaft 40 can additionally include an articulation joint 60 and rotation joint 70, discussed further below, coupled to a distal end 40d of the shaft 40.

In the illustrated embodiment, as shown in FIGS. 2 and 3, each of the end effector operational components can be coupled to components of the interface 20 and extend through the bore or lumen formed in the shaft 40, through the articulation joint 60 and rotation joint 70, and couple to the end effector 50. The shaft 40 can have a variety of sizes such that the instrument is well suited for use in various open, laparoscopic, or other minimally invasive procedures. In some embodiments, the shaft 40 can have an outer diameter in a range from about 5.0 mm to about 12.0 mm. Further, the shaft 40 can have any of a variety of cross-sectional shapes, including, for example, generally circular, ovoid, triangular, square, rectangular, etc. Additionally, the shaft 40 can be constructed from a variety of materials suitable for use in a surgical instrument. For example, in some embodiments the shaft can be formed from stainless steel, a glass reinforced polymer composite, or a thermoplastic extrusion. In some embodiments, and as illustrated in FIG. 2, the shaft 40 can include an articulation control 62 and the other above-described end effector operational components. The articulation control 62 and other end effector operational components can be disposed within the shaft 40 so that they are coaxially nested within the shaft, as shown in FIGS. 2 and 3. Further, both the articulation control 62 and the other end effector operational components can be configured to translate longitudinally relative to each other and the shaft 40, as described further below.

Turning to the partial view of FIG. 2 showing the various components disposed within the shaft 40 at staggered intervals and the cross-sectional view of FIG. 3, an inner-most conductor 30 is shown coaxially and centrally disposed within the lumen of the outer shaft 40. The conductor 30 can be one or more wires and can extend from the distal end 20d of the handle through the shaft 40. The conductor 30 can be a solid conductive cable, wire, or rod, or the wire can be a stranded wire or group of one or more separate wires. The conductor 30 can be covered with an electrically insulating material in some embodiments that can provide electrical isolation relative to the other components disposed thereabout. The conductor 30 can be configured to couple to the one or more electrodes 56 associated with at least one of the first, upper jaw 52 and the second, lower jaw 54 and can also couple to a power source, receptacle, or other component at a proximal end thereof in the interface 20. For example, the conductor 30 can be soldered to the one or more electrodes 56 at one end and soldered to a power source within the housing 22 of the interface 20 at the other end. Alternatively, the conductor 30 can be modularly and selectively coupled to the electrode 56 and the power source without soldering the wire, e.g., using any of a variety of modular electrical connectors. The conductor 30 can be disposed at any location with respect to the shaft 40 and can be configured to translate and rotate within the shaft 40, as shown, for example, in FIG. 3. The conductor can also be flexible enough to permit it to bend through any angle of articulation at the articulation joint 60. The conductor can also couple with a rotary contact at the proximal end of the shaft to allow for continuous rotation of the shaft (i.e., more than 360 degrees).

Figure 4:
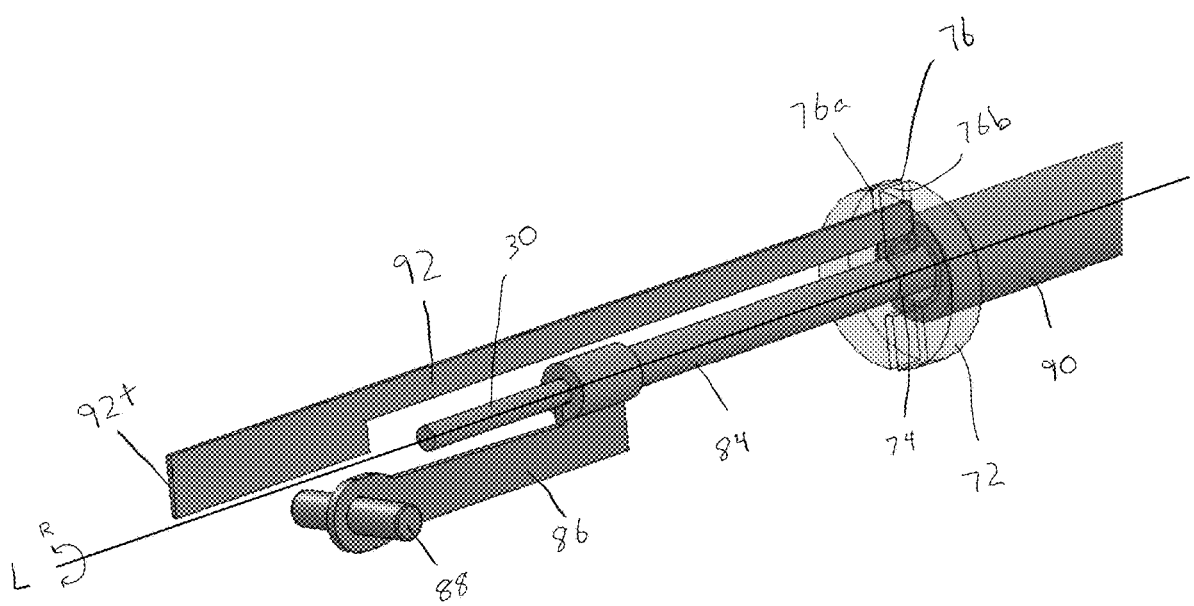
FIG. 4 is a partial perspective view of the surgical instrument of FIG. 1.

The jaw closure control 84, like the conductor 30, can be disposed within the lumen of the shaft 40. As in the illustrated embodiment, the jaw closure control 84 can be a shaft, cable, a non-conductive Vectran™ tube (Vectran™ is a multifilament manufactured fiber spun from a liquid crystal polymer, e.g., an aromatic polyester), or other element and can have a cylindrical shape with a central bore that runs from a proximal end to a distal end of the control 84, as shown in FIG. 3. Alternatively, the jaw closure control 84 may not have a bore, for example, in embodiments in which a conductor 30 is not present. In some embodiments, the jaw closure control 84 can be constructed of braided cable, a stranded Vectran™ cable, or alternatively from a reinforced polymer extrusion such as extruded plastic reinforced with steel. The jaw closure control 84 can extend from the distal end 20d of the handle 20 through the shaft 40, the articulation joint 60, and the rotation joint 70 to the end effector 50. As illustrated in FIG. 4, the distal end of the cable 84 can be coupled to a drive arm 86 and drive pin 88. The drive pin 88 can be adapted to engage opposed slots 53 formed in a jaw, e.g., the upper jaw 52 as shown in FIG. 5A and discussed further below. In the illustrated embodiment, as shown in FIGS. 2 and 3, the jaw closure control 84 can be disposed coaxially around the conductor 30 within the shaft 40. Regardless of how the control 84 is disposed within the shaft 40, it can be configured to both rotate and translate longitudinally within the shaft 40. The control 84 can also be flexible enough to permit it to bend through any angle of articulation at the articulation joint 60.

As shown in FIGS. 2 and 4, tissue transection can be accomplished using the cutting blade 92 that can be coupled to a transection control 90, which can be a shaft, cable, or other element similar to the jaw closure control 84. The blade 92 can include a distal tip 92t that can form a sharp edge conducive to cutting or transecting tissue. The transection control 90 can extend from the distal end 20d of the handle 20 through the shaft 40, the articulation joint 60, and rotation joint 70 to the end effector 50. In some embodiments, the transection control 90 can be an externally braided cable formed of stainless steel or titanium wire, or a composite braid formed from metal and an extruded polymer, e.g., polyether ether ketone (PEEK), Vectran™, or polytetrafluoroethylene (PTFE). The transection control 90 can include a central bore that runs from a proximal end to a distal end thereof. Alternatively, the transection control 90 can be formed without a bore in embodiments in which it represents a central-most coaxially disposed component. As with the conductor 30 and the jaw closure control 84, the transection control 90 can be configured to both translate and rotate relative to the shaft 40, and can be flexible enough to bend through any angle of articulation at the articulation joint 60. In certain embodiments, the larger diameter of the transection control 90 can reduce its flexibility and the material can be kerfed (i.e., periodic partial-thickness cutouts can be formed) to maintain desired flexibility of the shaft, cable, etc.

As in the embodiment shown in FIGS. 2 and 3, the end effector operational components can generally be coaxially and telescopically disposed within one another such that they can advance proximally and distally along the longitudinal axis L relative to the shaft 40 and relative to one another. For example, the conductor 30 can be coaxially disposed within the jaw closure control 84. The jaw closure control 84 can in turn be coaxially disposed within the transection control 90. In some embodiments, however, the order of coaxial nesting of the various components can be rearranged, e.g., as described below with respect to FIGS. 7 and 8. Moreover, in some embodiments certain components may be omitted, e.g., an instrument that does not include any of tissue sealing and transection functionality can omit any of the conductor 30 and transection control 90, respectively.

As shown in FIGS. 2 and 3, the end effector operational components 30, 84, 90 can be telescopically disposed within an articulation control 62. The articulation control 62 can be a cylindrical shaft, cable, or other member capable of exerting axial force in a "push/pull" manner on the articulation joint 60 to control actuation thereof. The articulation control 62 can extend from the distal end 20d of the interface 20 to the distal end 40d of the shaft 40 and can be coupled to the articulation joint 60. The articulation control 62 can be formed from any of a variety of materials, including, for example, PEEK, Vectran™, stainless steel tubing, or a glass reinforced extrusion composite. While the articulation control 62 can have some flexibility in certain embodiments, it can be sufficiently rigid to impart necessary force to the articulation joint 60 during use and, in some embodiments, need not have the flexibility of the other end effector operational components because it can terminate at the articulation joint 60 without passing therethrough. Moreover, in some embodiments the articulation control 62 can be configured to translate relative to the outer shaft 40 without rotating relative thereto. As a result, rotation of the other end effector operational components relative to the articulation control 62 and the shaft 40 can effect rotation of the end effector 50 via the rotation joint 70.

In still other embodiments, a separate rotation control (not shown) can be included at the interface 20 to control rotation of the outer shaft 40 and articulation control 62 relative to the interface 20 to allow the articulation joint 60 to rotate about the longitudinal axis L of the instrument 10. This additional rotation of the articulation joint 60 can extend the below-described articulation in a single plane about a hinge pin to any desired plane or direction. Incorporation of a such a feature would not inhibit rotation of the end effector 50 relative to the articulation joint 60 via the rotation joint 70 because the end effector operational components 30, 84, 90 extending through the articulation joint 60 remain rotatable and bendable relative thereto.

Figure 5C:
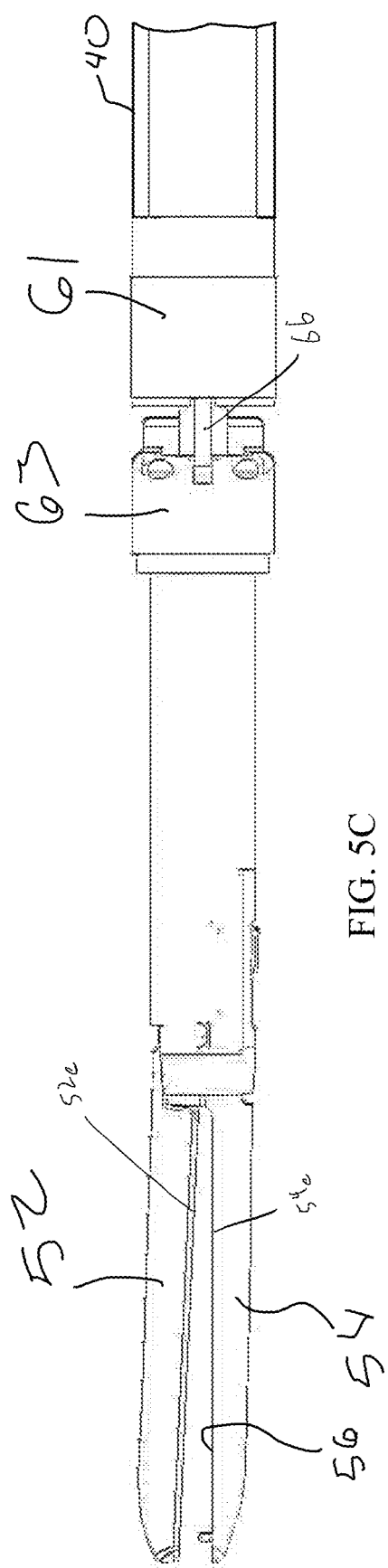
FIG. 5C is a partial side view of the surgical instrument of FIG. 1.

The end effector 50 can have a variety of sizes, shapes, and configurations. In the illustrated embodiment, and as shown in more detail in FIGS. 5A-5D, the end effector 50 can include a first, upper, or top jaw 52 and a second, lower, or bottom jaw 54 disposed at a distal end of the articulation joint 60 and rotation joint 70. The upper jaw 52 and the lower jaw 54 can be curved, or concave, as shown in FIG. 5B. For example, the end effector 50 can include a Maryland-type jaw. In the illustrated embodiment, the jaws 52, 54 can have a substantially elongate shape with a curve along the longitudinal axis $L_E$ of the end effector 50, though a variety of other shapes can be used to form the jaws 52, 54, including jaws that are substantially elongate and substantially straight and configurations that are not necessarily congruent with respect to the opposed jaws across the duration of the length of the jaws. Further, the jaws 52, 54 can have any suitable axial length for engaging tissue, where the axial length is measured along the longitudinal axis $L_E$ of the end effector 50. The axial length of the jaws 52, 54 can also be selected based on the targeted anatomical structure for transection and/or sealing. Still further, the jaws 52, 54 can also include an elongate channel 94 (see FIG. 5B showing the channel for the jaw 52; not illustrated for the jaw 54) extending between the two jaws to form a path through which the cutting blade 92 can traverse.

As shown, the second jaw 54 can be coupled to the proximal body portion 50p of the end effector 50 so that it is relatively fixed with respect to the proximal body portion 50p, and the first jaw 52 is pivotally coupled to the second jaw 54 to allow the jaws to be opened and closed with respect to each other. The first jaw 52 can include opposed slots 53 formed in a proximal end thereof such that distal and proximal movement of the jaw closure control 84, and more specifically the drive pin 88 disposed within the slots 53 and coupled to the control 84 via the drive arm 86, results in the upper jaw pivoting between open and closed configurations. In an open configuration, the jaws 52, 54 can be spaced a distance apart from one another, while in a closed configuration, the jaws can be substantially close to one another so that tissue-engagement surfaces $52_e$, $54_e$ of the jaws 52, 54, respectively, are approximately parallel to each other and to the longitudinal axis $L_E$ extending through the end effector 50. In other embodiments, the lower jaw 54 can be configured to pivot while the upper jaw 52 remains substantially stationary, or both jaws 52, 54 can move equally relative to, e.g., the longitudinal axis $L_E$ of the end effector 50.

As noted above, the end effector 50 can include a cutting blade 92 for transecting tissue disposed between the jaws 52, 54. A length of the proximal portion 50p of the end effector 50 can be a function of the length of the blade 92, as the proximal portion of the end effector can be configured to house the blade when it is retracted proximally relative to the jaws 52, 54. In some embodiments, a proximal portion 50p of the end effector 50 can have a runway length X sufficient to receive the retracted blade 92 such that it does not inadvertently contact tissue grasped by the jaws. In some embodiments, the runway length X can be in a range from about 15.0 mm to about 25.0 mm. For example, in one embodiment the runway length X can be about 20.0 mm. In other embodiments, the blade 92 can be omitted and any required tissue transection can be performed using a separate instrument. In such embodiments, the length of the end effector 50, and especially the proximal portion 50p thereof, can be reduced because there is no need for runway length to accommodate a retracted blade at a position distal of the articulation joint 60 and proximal to the jaws 52, 54.

The jaws 52, 54 can have any combination of features configured to facilitate tissue grasping. For example, any of the engagement surfaces $52_e$, $54_e$ of the jaws 52, 54 can include one or more surface features formed thereon that can help secure the tissue. The surface features can include, by way of non-limiting example, any of teeth, ridges, or depressions configured to increase friction between the tissue and the engagement surfaces, without tearing or otherwise damaging the tissue contacting such surface features.

Additionally, any of the tissue-engagement surfaces of the upper and lower jaws 52, 54 can include one or more electrodes 56 disposed thereon. As shown, one or more electrodes 56 can be disposed on the tissue-engagement surface 54$_e$ of the lower jaw 54 and can be generally configured to supply energy to tissue disposed between the jaws 52, 54 to coagulate or seal the tissue. The one or more electrodes 56 can be coupled to the tissue-engagement surface 54$_e$ of the jaw 54 using any suitable manner, including, by way of non-limiting example, using an adhesive. In some exemplary embodiments, the one or more electrodes 56 can include a positive temperature coefficient (PTC) polymer or matrix that can provide more homogeneous and precisely regulated energy delivery with lower thermal spread. The PTC conductive-resistive matrix can be a variably resistive body that comprises a polypropylene or a medical grade silicone polymer that is doped with conductive particles (e.g., carbon). Certain polymer PTC materials are known in the field as over current protection devices that can "trip" and become resistant when a selected temperature is exceeded. Although the one or more electrodes 56 are illustrated in association with the lower jaw 54 in FIGS. 5A and 5C, in other embodiments one or more electrodes can be disposed on the upper jaw 52 in addition to, or in place of, the one or more electrodes 56 disposed on the lower jaw 54. Any number of electrodes can be used on either jaw 52, 54 and, in some embodiments, electrodes can be omitted entirely.

More generally, the illustrated embodiment of the surgical instrument 10 provides one of many possible instrument configurations and associated methods of use that are consistent with the teachings provided herein. A variety of other surgical instrument configurations are also possible. For example, in some embodiments a device can be configured to apply staples to tissue in addition to, or in lieu of, any of cutting or sealing tissue. Some non-limiting examples of other device configurations that can be used in conjunction with the present disclosure, and their related methods of use, include the disclosures provided for in U.S. Patent Application Publication No. 2012/0083835 and U.S. Patent Application Publication No. 2013/0161374, each of which is incorporated by reference in its entirety. Further, in some embodiments an end effector may not include a jaw assembly at all. In such embodiments, the above-described jaw closure control 84 can more generally be referred to as an end effector function control that can be configured to actuate a function that the end effector is designed to perform.

Returning to FIGS. 5A-5D, the articulation joint 60 can be disposed between the outer elongate shaft 40 and the end effector 50 and can be configured to enable the end effector 50 to move at angles with respect to the central longitudinal axis L of the elongate shaft 40 so that the end effector 50 can be articulated to any position between a substantially straight configuration (e.g., wherein the longitudinal axis L of the instrument 10 and the longitudinal axis L$_E$ of the end effector are aligned) and a fully articulated configuration (e.g., wherein the longitudinal axis L of the instrument 10 and the longitudinal axis L$_E$ of the end effector are perpendicular to one another) via translation of the articulation control 62. The articulation joint 60 provided for herein can utilize an offset hinge, as described below, to allow a single articulation control 62 to actuate the joint via proximal or distal translation. In an alternative embodiment, the device 10 can include multiple articulation controls, such as controls disposed oppositely from one another, to allow for articulation of the end effector using an opposed "push/pull" actuation of the controls.

The articulation joint 60 can include a rotation joint 70 in some embodiments. The rotation joint 70, in combination with the articulation joint 60 and the flexible coaxially disposed end effector operational components, can advantageously provide for both consistent articulation and rotation of an end effector 50, regardless of its position. More particularly, the joints 60, 70 can provide a device capable of articulating an end effector 50 to access tissue, and subsequently rotating the end effector about a longitudinal axis L$_E$ thereof (i.e., rotating the end effector 50 distal of the articulation joint 60). Such complex movements have been impossible in prior devices due to twisting, kinking, or buckling of control elements, or have required substantially more complex configurations to achieve such capability.

The articulation joint 60 can include a first, proximal joint member 61 and a second, distal joint member 63 pivotally connected to allow the end effector 50 to be articulated. One exemplary embodiment of the articulation joint 60 is illustrated in detail in FIGS. 5A-5D. As shown in FIG. 5C, the proximal joint member 61 can be in the form of a tube-like structure secured relative to the shaft 40. Alternatively, the proximal joint member 61 can be in the form of a plate or bracket affixed to the distal end of the shaft 40. The distal joint member 63 can similarly be generally tube shaped and include a cut out on a proximal face 63p that is at an angle relative to a plane P that is perpendicular to the longitudinal axis L of the device 10. The angle of the proximal face 63p relative to the plane P can be in a range from about 45 degrees to about 60 degrees. The angle of the proximal face 63p can be chosen to achieve a desired angle of articulation of the device 10. The proximal face 63p can serve as a stop to prevent over articulation of the end effector 50. For example, the proximal face 63p can abut, or come into contact with, the distal face 61d of the proximal member 61, thereby preventing further articulation.

Figure 5D:
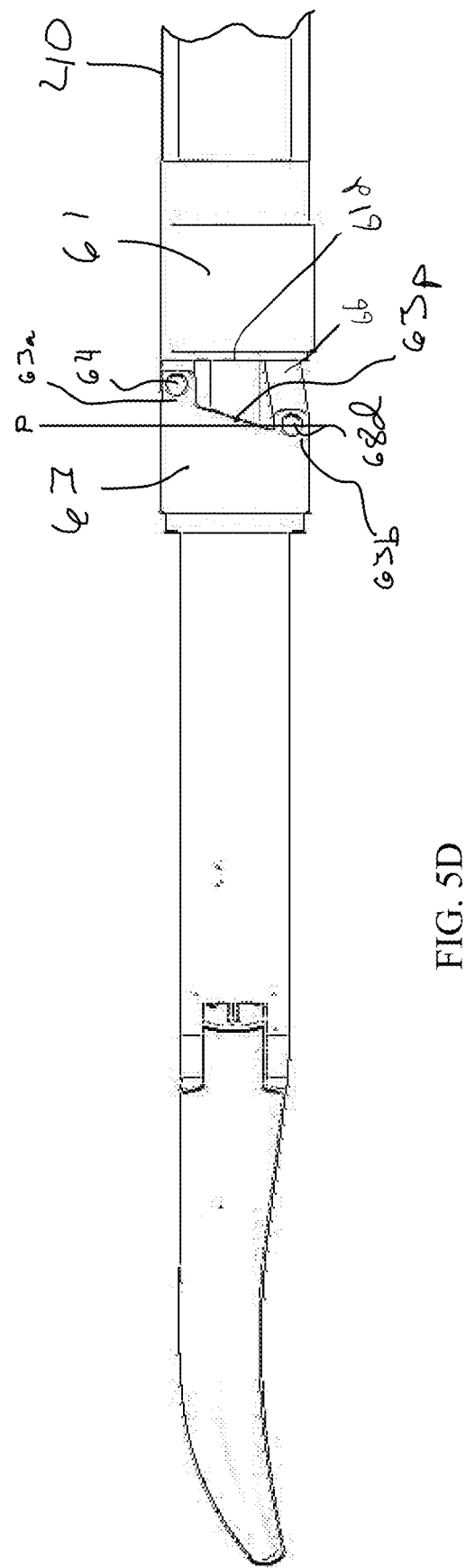
FIG. 5D is a partial top view of the surgical instrument of FIG. 1.

The distal joint member 63 can be pivotally connected to the proximal joint member 61 at one location and connected to the articulation control 62 at another location. In one embodiment, as shown in FIGS. 5B and 5D, the connections to the proximal member 61 and the articulation control 62 can be oppositely offset, i.e., rotationally offset approximately 180 degrees, from one another and can be disposed along an outer circumference of the articulation joint 60. Such placement can maximize the mechanical advantage of the articulation joint 60 while minimizing its size and maintaining a central lumen for the end effector operational components to pass through. More particularly, in the illustrated embodiment the proximal member 61 can be connected, at a first location 63a, to the distal member 63 by means of a hinge pin 64. In the illustrated embodiment, the location of the hinge pin 64, relative to the device 10, can be longitudinally fixed by the proximal member 61 in both the articulated configuration and the unarticulated configuration of the end effector. The hinge pin 64 can therefore be disposed at one position along the length of the device 10. The articulation control 62 can be pivotally connected to the distal member 63 at a second location 63b. As in the illustrated embodiment, the articulation control 62 can be connected to the distal member 63 by means of an elongate link member 66. The link member 66 can be pivotally connected to both the distal member 63 and the distal end of the articulation control 62 by means of pins 68*d*, 68*p*, respectively. The length L₁ of link 66, in addition to the angle of the proximal face 63*p*, can be selected to achieve the desired range of movement of the articulation joint 60. The link 66 can translate within a slot or guide 65 extending proximally from a distal end of the proximal member 61. The pin 68*d* can connect the link member 66 to the distal member 63 at a location along the longitudinal axis L of the device 10 that is offset from the hinge pin 64, as shown in FIGS. 5B and 5D. Alternatively, the hinge pin 64 and pin 68*d* can be disposed at the same, or substantially the same location along the longitudinal axis L of the device 10.

In an exemplary method of use, the actuation lever 28 on the handle 20 can be manipulated to articulate the end effector 50 about the pivot pin 64 from an unarticulated configuration, as shown in FIG. 6A, to an articulated configuration, as shown in FIG. 6B. Upon actuation of the articulation lever 28, the articulation control 62 can be translated or "pulled" proximally along the length L of the device 10 with the force F1. As the articulation control 62 is translated proximally, the distal end 62*d* of the articulation control can retract the link 66 proximally to bring the proximal face 63*p* of the distal member 63 towards the proximal member 61, as shown in FIG. 6B. The link 66 can transfer the force F1 of the articulation control 66 to the distal member 63, causing the distal member 63, and thereby the end effector 50, to pivot about hinge pin 64 in a first direction P1. In some embodiments, the articulation can cause the link 66 to extend beyond the inner diameter of the lumen of the shaft 40 and/or proximal member 61. In such a case, the slot or guide 65 formed in the proximal member 61 can receive the link 66.

To return the end effector 50 to the aligned configuration of FIG. 6A, the articulation lever 28 can be manipulated to distally translate or "push" the articulation control 62 towards the distal end of the shaft 40*d*. This translation can pivot the distal member 63 in a second direction P2 toward the configuration of FIG. 6A. In some embodiments, articulation in an opposite direction, i.e., toward the configuration shown in FIG. 6C, can be accomplished by further advancing the articulation control distally to pivot the distal member 63 in the second direction P2 to the configuration shown in FIG. 5C. Accordingly, the articulation control shaft, cable, or other element can function as a push-pull mechanism to move the end effector about the hinge pin. In some embodiments, articulation in the second direction P2 can be limited by interference between the link member 66 and the end effector operational components (not shown in FIG. 6C, see transection control 90 shown in FIG. 6A) disposed within an inner lumen of the articulation control 62. Accordingly, in certain embodiments, such as those employing Maryland-type jaws that curve in one direction, articulation in the direction of the curve can be favored and a greater degree of movement can be possible.

In an alternative embodiment, the articulation joint 60 can include dual articulation controls that can each be coupled to the distal member 63 via a hinge pin. In such an embodiment, the first and second articulation controls can be used in an alternating "push/pull" configuration to pivot the end effector 50 in the opposite directions P1, P2. For example, the first articulation control can be translated proximally while maintaining a position of (or advancing distally) the second articulation control to pivot the end effector 50 in the first direction P1. Conversely, the second articulation control can be translated proximally while maintaining a position of (or advancing distally) the first articulation control to pivot the end effector 50 in the second direction P2. The first and second articulation controls can be coaxially disposed, one within the other.

The rotation joint 70 can be disposed at a proximal end 50*p* of the end effector 50 where the end effector interfaces with the distal joint member 63 and can be configured to guide rotation of the end effector 50. Advantageously, the rotation joint 70 can allow for articulation and rotation of the end effector 50 without the need for slip rings or other structures to maintain a continuous electrical path for the conductor 30 through the articulation joint 60 to the end effector 50. Rather, a single length of wire (e.g., conductor 30) can extend from the interface 20 to the end effector 50 in some embodiments. Twisting or other deformation is not a concern because the conductor 30 (and other end effector operational components) rotate with the end effector to maintain a constant relative alignment. More particularly, the conductor 30, as well as the coaxially disposed jaw closure control 84 and transection control 90, can couple at a distal end thereof to the end effector 50 and can be configured to rotate therewith to avoid any twisting, kinking, or other deformation during rotation maneuvers. Moreover, these components can be flexible enough to bend through the articulation joint 60 when the end effector is articulated away from the aligned configuration of FIG. 6A to the articulated configurations of FIGS. 6B and 6C. Indeed, in some embodiments rotation of the end effector 50 relative to the articulation joint 60 and shaft 40 can be controlled by rotating any of the conductor 30, jaw closure control 84, and transection control 90 independently or in unison.

To aid in aligning the various components of the end effector 50 during rotation (and to permit rotation of a single such component to control rotation of all), a guide 72 can be disposed at a distal end of the transection control 90, as shown in FIGS. 4-5B. In the illustrated embodiment, the guide 72 can be a substantially cylindrical body having a central bore 74 and at least one radially extending through slot 76, though a variety of other shapes and configurations are also possible. The guide 72 can be disposed in the proximal portion 50*p* of the end effector 50 so that the guide can rotate about and translate along the longitudinal axis $L_E$ with the transection control 90. Further, the blade 92 extending from a distal end of the transection control 90 can be received within the slot 76 such that the guide 72 can help maintain alignment of the blade 90. The guide 72 can also serve to prevent buckling of the blade 92 during transection as it is advanced distally through tissue.

In an alternative embodiment, the guide 72 can be fixed to the jaw closure control 84 so that axial movement of the jaw closure control can axially translate the guide within the end effector 50. For example, the jaw closure control 84 can be fixedly disposed within the bore 74 of the guide 72. The drive arm 86, including drive pin 88, can fixedly extend from a distal end of the jaw closure control 84. Proximal and/or distal movement of the jaw closure control 84 can drive corresponding movement of the drive arm 86, and thus the drive pin 88, to move the drive pin 88 in a proximal or distal direction along the longitudinal axis $L_E$. In such an embodiment, proximal or distal movement of the jaw closure control 84 can also cause corresponding movement of the guide 72, and the slot 76 can be sized such that the blade 92 can be received therein and supported while allowing for relative translation between the guide and the blade.

The guide 72 can ensure co-rotation of the end effector operational components while permitting independent translational movement thereof. For example, in an embodiment in which the blade 92 is fixedly attached to a distal end of the transection control 90 and the guide 72 is attached to the jaw closure control 84, rotation of either component can cause corresponding rotation of the other due to the blade 92 being received within the slot 76. Despite this rotational coupling, any of the transection control 90 (and blade 92) and jaw closure control 84 can be proximally or distally translated along the longitudinal axis $L_E$ without causing any corresponding movement of the other component. By way of further example, in one embodiment the rotation control 78 of the interface 20 can rotate the transection control 90 about the longitudinal axis L in the rotational direction R, as shown in FIG. 3. Rotation of the transection control 90 can cause the blade 92, disposed through the slot 76, to rotate. As the blade 92 is rotated, in the direction R about the longitudinal axis L, the blade 92 can bear against one of the side walls 76a, 76b, of the slot 76 so as to co-rotate the guide 72 therewith. The rotation of the guide 72 can cause rotation of the end effector 50 relative to the shaft 40 and articulation joint 60. Actuation of the rotation control 78 can also be transferred to the jaw closure control 84 due to its coupling with any of the end effector jaws (via the drive arm 86 and the drive pin 88) and the guide 72. Accordingly, there are a number of different configurations by which actuation of a rotation control 78 can effect rotation of the end effector relative to the articulation joint 60 and shaft 40. Moreover, in each such embodiment the end effector operational components extending through the shaft 40 and articulation joint 60 to the end effector 50 can be configured to rotate with the end effector, thereby eliminating concerns regarding twisting or other deformation due to such movement. Moreover, the end effector operational components can be flexible enough to bend and rotate through the articulation joint 60 at any degree of articulation. As a result, the end effector 50 can be actuated to rotate either before, during, or after the end effector 50 has been articulated about the joint 60.

Figure 7:
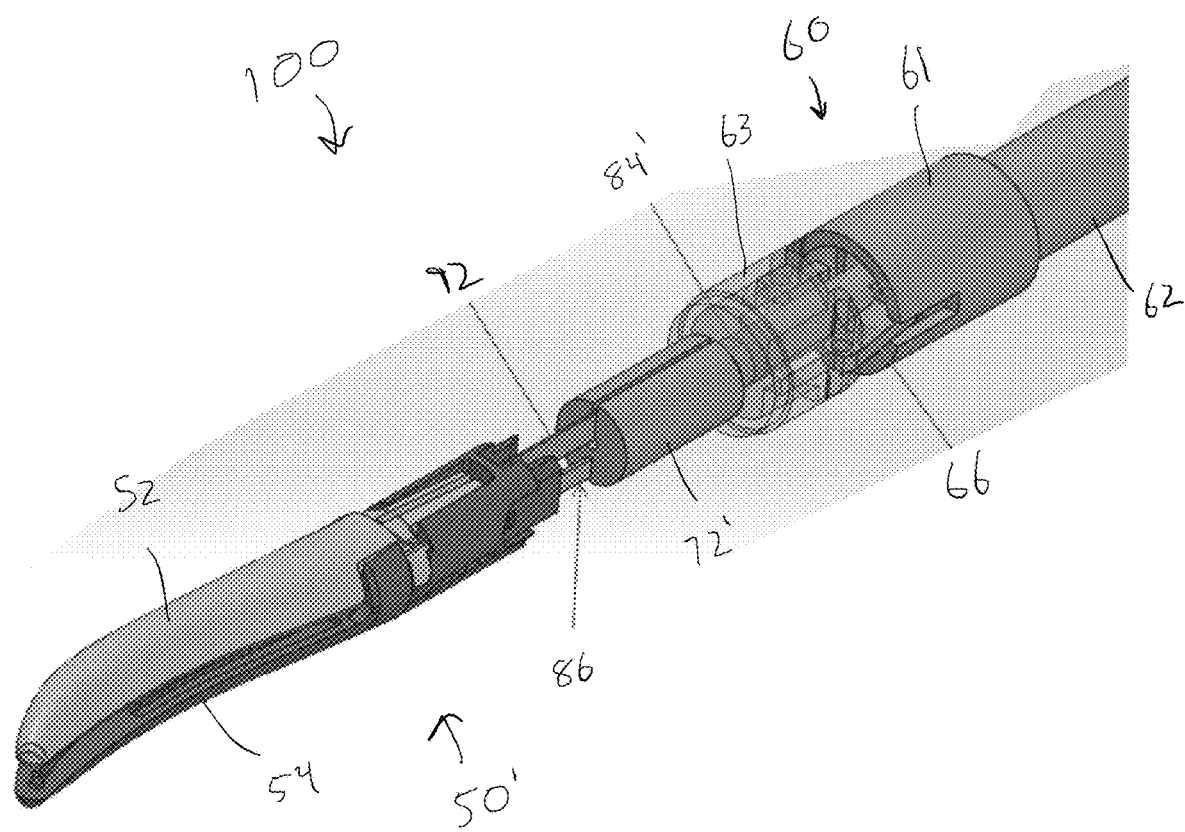
FIG. 7 is a partial perspective view of another embodiment of a surgical instrument according to the teachings of the present disclosure.
Figure 8:
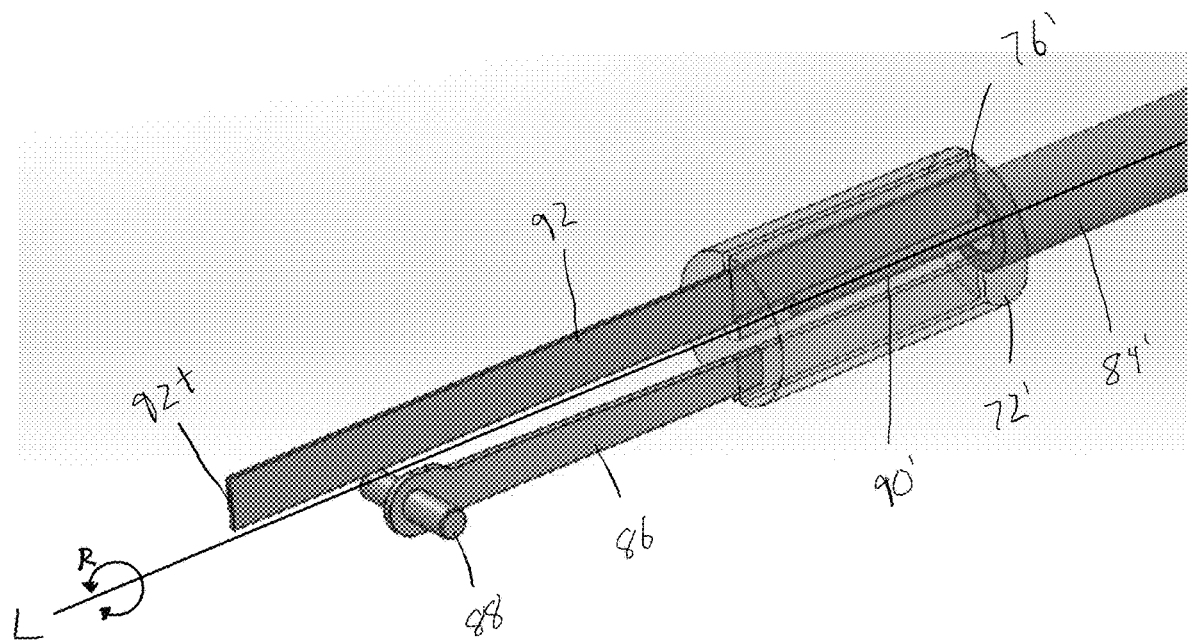
FIG. 8 is a partial detail view of the surgical instrument of FIG. 6.

The above described features of the surgical instrument 10 are one example of an embodiment according to the teachings provided herein. A number of alternative embodiments are possible and within the scope of the present disclosure. FIGS. 7 and 8 illustrate one such alternative embodiment in which nesting of the various end effector operational components is changed. For example, in the partial perspective view of FIG. 7 an instrument 100 is shown that includes an end effector 50' having jaws 52, 54 just like the end effector 50 described above. The instrument 100 can also include an articulation joint 60 that can itself include a proximal joint member 61, a distal joint member 63, a hinge pin (not visible), and an elongate link member 66 offset from the hinge pin and coupled to a distal end of an articulation control shaft 62.

As shown in the detail view of FIG. 8, however, the instrument 100 can include a configuration of end effector operational components in which a transection control 90' is disposed within an inner lumen of a jaw closure control 84', which is opposite the configuration shown in FIG. 4. In such an embodiment, the blade 92 can be coupled to the transection control 90' and the drive arm 86 can be coupled to the jaw closure control 84'. An alternative embodiment of a guide 72' is also shown having a greater axial length than the guide 72 shown in FIG. 4. The greater axial length can provide additional surface area for imparting forces to other components to, e.g., cause alignment of rotation or ensure axial alignment of the blade, etc. The guide 72' can be coupled to the jaw closure control 84' and drive arm 86 and can include a slot 76' to receive the blade 92. In such a configuration, the guide 72 can serve a similar purpose of ensuring simultaneous rotation of the transection control 90' and the jaw closure control 84', any of which can cause rotation of the end effector 50' about a longitudinal axis thereof. At the same time, independent translation of each of these components can be permitted to effect, e.g., jaw closure, tissue transection, or other end effector functions.

In addition to the above-described surgical instruments, also contemplated are various methods of utilizing these and other instruments that employ articulating portions according to the teachings provided herein. Such methods can include, for example, introducing any of the above-described instruments or devices into a patient's body, articulating an end effector to access a surgical site, rotating the end effector about a longitudinal axis thereof, as well as grasping, sealing, and transecting tissue. Also contemplated are methods of producing the coaxial end effector operational components described herein, including, for example, processes of co-extrusion and over-molding that can be utilized to form end effector operational components having an inner component formed from a first material and an outer component formed from a second material.

In one embodiment for example, a surgical method according to the teachings of the present disclosure can include articulating an end effector relative to a shaft by translating a single articulation control that is coaxially disposed within the shaft. The articulation control can be, for example, a second shaft coaxially disposed within a lumen of the shaft. The method can further include rotating the end effector about a longitudinal axis thereof by rotating an actuating control coaxially disposed within the articulation control shaft. The actuating control can be, for example, a cable disposed within a lumen of the articulation control shaft. The method can also include actuating an end effector function by translating the actuating cable. The end effector function can be, for example, closing opposed end effector jaws, advancing a blade to transect tissue, etc. In some embodiments, a second actuating control, such as a second actuating cable, can be coaxially disposed within the actuating cable and can be utilized to actuate a second end effector function. Finally, in some embodiments the method can further include delivering energy to tissue grasped by the first and second jaws through a conductor coaxially disposed within any of the actuating cables. Still further, in any of the above examples the various actuating controls or cables and the conductor can be configured to both bend and rotate through an articulation joint such that the coaxial drive can continue to effect rotation and actuation of the end effector via rotation and translation of the various coaxial drive components.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present disclosure.

The instruments described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the instrument due to the materials utilized, the presence of electrical components, etc.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated by reference in their entirety.

What is claimed is:

1. A surgical instrument, comprising:
   a shaft having a proximal end, a distal end, and lumen extending therethrough;
   an end effector coupled to the distal end of the shaft by an articulation joint such that the end effector can articulate relative to a longitudinal axis of the shaft and can rotate about a longitudinal axis of the end effector;
   a first actuating cable coaxially disposed within the lumen of the shaft and extending through the articulation joint to the end effector,
   a second actuating cable coaxially disposed within the first actuating cable and extending through the articulation joint to the end effector,
   an articulation control shaft coaxially disposed within the lumen of the shaft and configured to translate proximally and distally to articulate the end effector relative to the longitudinal axis of the shaft;
   wherein the first and second actuating cables are configured to bend and rotate through the articulation joint; and
   wherein rotation of the first actuating cable relative to the second actuating cable is configured to control rotation of the end effector about a longitudinal axis thereof, and translation of the first actuating cable relative to the second actuating cable is configured to translate a blade to transect tissue grasped by the end effector.

2. The instrument of claim 1,
   wherein the end effector includes a first jaw and a second jaw pivotally coupled to one another and movable between an open configuration and a closed configuration; and
   wherein translation of the second actuating cable relative to the first actuating cable is configured to move the first and second jaws between the open and closed configurations.

3. The instrument of claim 2, further comprising a drive arm and drive pin coupled to a distal end of the second actuating cable, the drive pin being configured to engage opposed slots formed in one of the first or second jaws such that, upon distal translation of the second actuating cable relative to the first actuating cable, the drive pin engages the opposed slots to cause the first and second jaws to move between the open configuration to the closed configuration.

4. The instrument of claim 2, wherein translation of the first actuating cable relative to the second actuating cable is configured to only translate the blade, and translation of the second actuating cable relative to the first actuating cable is configured to only move the first and second jaws between the open and closed configurations.

5. The instrument of claim 1,
   wherein the end effector includes a first jaw and a second jaw pivotally coupled to one another and movable between an open configuration and a closed configuration, and the blade is configured to translate proximally and distally relative to the first and second jaws.

6. The instrument of claim 5, wherein the second actuating cable is configured to translate proximally and distally to move the first and second jaws between the open and closed configurations.

7. The instrument of claim 5, further comprising a conductor coaxially disposed within the second actuating cable and configured to deliver energy to the end effector.

8. The instrument of claim 1, wherein the articulation control shaft is coaxially disposed about the first actuating cable within the lumen of the shaft.

9. The instrument of claim 1,
   wherein the articulation joint includes a distal portion rotatably coupled to the end effector and a proximal portion coupled to the shaft; and
   wherein the distal portion is coupled to the proximal portion by a hinge pin that is offset from the longitudinal axis of the shaft.

10. The instrument of claim 9, wherein the articulation control shaft is coupled to the distal portion of the articulation joint at a position oppositely offset from the longitudinal axis of the shaft.

11. The instrument of claim 9, wherein the hinge pin is positioned along an outer circumference of the articulation joint.

12. The instrument of claim 9, further comprising an elongate link extending between the articulation control shaft and the distal portion of the articulation joint.

13. The instrument of claim 12, wherein the proximal portion of the articulation joint includes a slot extending proximally from a distal end thereof and sized to receive the elongate link when the end effector is articulated relative to the shaft.

14. The instrument of claim 12, wherein the hinge pin is positioned proximal to a distal end of the elongate link when the longitudinal axis of the end effector is aligned with the longitudinal axis of the shaft.

15. The instrument of claim 1, further comprising an interface coupled to the proximal end of the shaft and configured to control rotation and translation of the first and second actuating cables.

16. The instrument of claim 15, wherein the interface is configured for use with a surgical robot.

17. The instrument of claim 1, further comprising a conductor coaxially disposed within the second actuating cable through the articulation joint and configured to deliver energy to the end effector, the conductor being configured to translate within the second actuating cable relative to the first and second actuating cables, the conductor being configured to rotate with the end effector to maintain a constant relative alignment between the end effector and the conductor.

18. The instrument of claim 1, further comprising a guide disposed at a proximal end of the end effector and in engagement with a distal end of the first actuating cable, the guide being configured to indicate an alignment of the first actuating cable, the guide having a cylindrical body and at least one radially extending through slot, and the blade being received within the through slot such that the guide is configured to maintain alignment of the blade.

19. A surgical instrument, comprising:
an elongate cylindrical housing having a proximal end, a distal end, and a lumen extending the through along a longitudinal axis;
an end effector coupled to the distal end of the housing by a hinge mechanism including a hinge pin that is offset from the longitudinal axis of the housing;
first and second coaxial members extending through the lumen and the hinge mechanism to the end effector, the second coaxial member being coaxially disposed within the first coaxial member,
wherein the surgical instrument has a first configuration in which the elongate cylindrical housing and the end effector are substantially coaxially aligned, and a second configuration in which the end effector is pivoted relative to the elongate cylindrical housing such that the end effector is angularly offset from the longitudinal axis;
wherein the first and second coaxial members are configured to bend and rotate within the hinge mechanism when the surgical instrument is in the second configuration; and
wherein rotation of the first coaxial member is configured to rotate the end effector relative to the elongate cylindrical housing, translation of the first coaxial member is configured to cause translation of a knife along the end effector, and translation of the second coaxial member is configured to cause capture of tissue by the end effector.

20. The surgical instrument of claim 19, wherein the hinge mechanism includes a push-pull mechanism.

21. The surgical instrument of claim 20, wherein the push-pull mechanism includes a distal end and a proximal end and is coaxially disposed between the housing and the first coaxial member.

22. The surgical instrument of claim 21,
wherein the hinge pin pivotally connects a first side of the end effector to the housing, and the hinge mechanism further includes a second hinge pin pivotally connecting a second side of the end effector to the push-pull mechanism; and
wherein the hinge pin is proximal to the second hinge pin when the instrument is in the first configuration.

23. The surgical instrument of claim 22, wherein the hinge mechanism includes an elongate link disposed between the second hinge pin and the distal end of the push-pull mechanism.

24. The surgical instrument of claim 20, wherein the push-pull mechanism is configured to actuate the surgical instrument from the first configuration to the second configuration with substantially linear movement of the push-pull mechanism.

25. The surgical instrument of claim 19, wherein the end effector includes a grasper; and
wherein the second coaxial member is configured to actuate the grasper to capture the tissue.

26. The surgical instrument of claim 25, wherein the first and second coaxial members are configured to slide along the longitudinal axis within the elongate cylindrical housing and the hinge mechanism while the surgical instrument is in the second configuration to actuate the grasper and the knife.

27. The surgical instrument of claim 25, further comprising a substantially cylindrical guide disposed around the second coaxial member and connected to a grasper actuation link, the guide having a slot extending therethrough for receiving a distal end of the knife such that the knife can slide within the slot.

28. A surgical method, comprising:
articulating an end effector relative to a shaft about an articulation joint by translating a single articulation control shaft coaxially disposed within the shaft;
rotating the end effector about a longitudinal axis thereof by rotating a first actuating cable coaxially disposed within the articulation control shaft and extending through the articulation joint to the end effector;
translating a blade along the end effector by translating the first actuating cable; and
causing the end effector to capture tissue by translating a second actuating cable coaxially disposed within the first actuating cable and extending through the articulation joint to the end effector.

29. The method of claim 28, wherein translating the second actuating cable causes movement of first and second jaws of the end effector to capture the tissue.

30. The method of claim 29, further comprising delivering energy to tissue grasped by the first and second jaws through a conductor coaxially disposed within the second actuating cable.

* * * * *